(12) United States Patent
Yates et al.

(10) Patent No.: US 6,497,236 B1
(45) Date of Patent: Dec. 24, 2002

(54) COMBINATION TOOTHBRUSH HOLDER AND DENTAL FLOSS DISPENSER

(76) Inventors: Davis V. Yates, 1826 Stonecrest Ct., Lakeland, FL (US) 33813; Charles H. Howell, 1826 Stonecrest CT., Lakeland, FL (US) 33813

( * ) Notice: Subject to any disclaimer, the term of this patent is extended or adjusted under 35 U.S.C. 154(b) by 266 days.

(21) Appl. No.: 09/696,404

(22) Filed: Oct. 25, 2000

(51) Int. Cl.[7] ............................................. A45D 44/00
(52) U.S. Cl. .................... 132/309; 220/521; 211/65; 248/111
(58) Field of Search ................................ 132/309, 310; 248/110, 111, 113, 314; 206/362.1, 362.2, 362.3, 15.2, 15.3; 211/65, 66; D6/527, 528; 220/521, 23.87, 23.86, 23.83

(56) References Cited

U.S. PATENT DOCUMENTS

| | | | | |
|---|---|---|---|---|
| 253,268 A | * | 2/1882 | Dowling | 220/573.4 |
| 1,849,769 A | * | 3/1932 | Priest | 132/309 |
| 2,211,326 A | * | 8/1940 | Gillace | 220/8 |
| 4,673,106 A | | 6/1987 | Fishman | |
| 4,978,003 A | | 12/1990 | Foster | |
| 5,097,964 A | | 3/1992 | Fitz | |
| D336,398 S | * | 6/1993 | Shafer | D6/534 |
| 5,215,193 A | | 6/1993 | Dennis | |
| 5,335,798 A | | 8/1994 | Bonwell et al. | |
| 5,490,722 A | | 2/1996 | Sonnett et al. | |
| 5,515,991 A | * | 5/1996 | Heitland | 220/256 |
| 5,551,590 A | * | 9/1996 | Mazur et al. | 220/465 |
| 5,638,840 A | | 6/1997 | Lee et al. | |
| 5,662,130 A | | 9/1997 | Wiltshire | |
| 5,765,739 A | | 6/1998 | Yates, III | |
| 5,924,429 A | | 7/1999 | Morando | |
| 6,047,712 A | * | 4/2000 | Blades et al. | 132/325 |
| D425,349 S | | 5/2000 | Adkins | |
| D428,288 S | * | 7/2000 | Mahlmann | D6/534 |
| D443,158 S | * | 10/2000 | Ng | D6/534 |
| 6,186,324 B1 | * | 2/2002 | Catterson | 206/362.1 |

* cited by examiner

Primary Examiner—Todd E. Manahan
Assistant Examiner—David C Comstock
(74) Attorney, Agent, or Firm—Larson & Larson, P.A.; James E. Larson

(57) ABSTRACT

A frusto-conical member has a planar rim disposed at a bottom closed end and a circular open portion disposed at a top end. A lid having a plurality holes formed therethrough inserts over the frusto-conical open portion and is retained by friction. An elongated portion of a toothbrush is inserted through one of the holes formed in the lid for retaining the toothbrush in an upright position such that bristles of the toothbrush are exposed to the ambient air. A grommet having a center aperture is inserted into one of the holes in the lid. Disposed underneath the grommet is a small housing for retaining a source of dental floss. The housing includes a cover having a tip portion which inserts through the grommet aperture. The source of dental floss threads through the tip portion and out through the grommet aperture. A small cutter element is disposed along an outer circumference of the frusto-conical member below the grommet and is used to cut a strand of desired length from the source of dental floss.

20 Claims, 4 Drawing Sheets

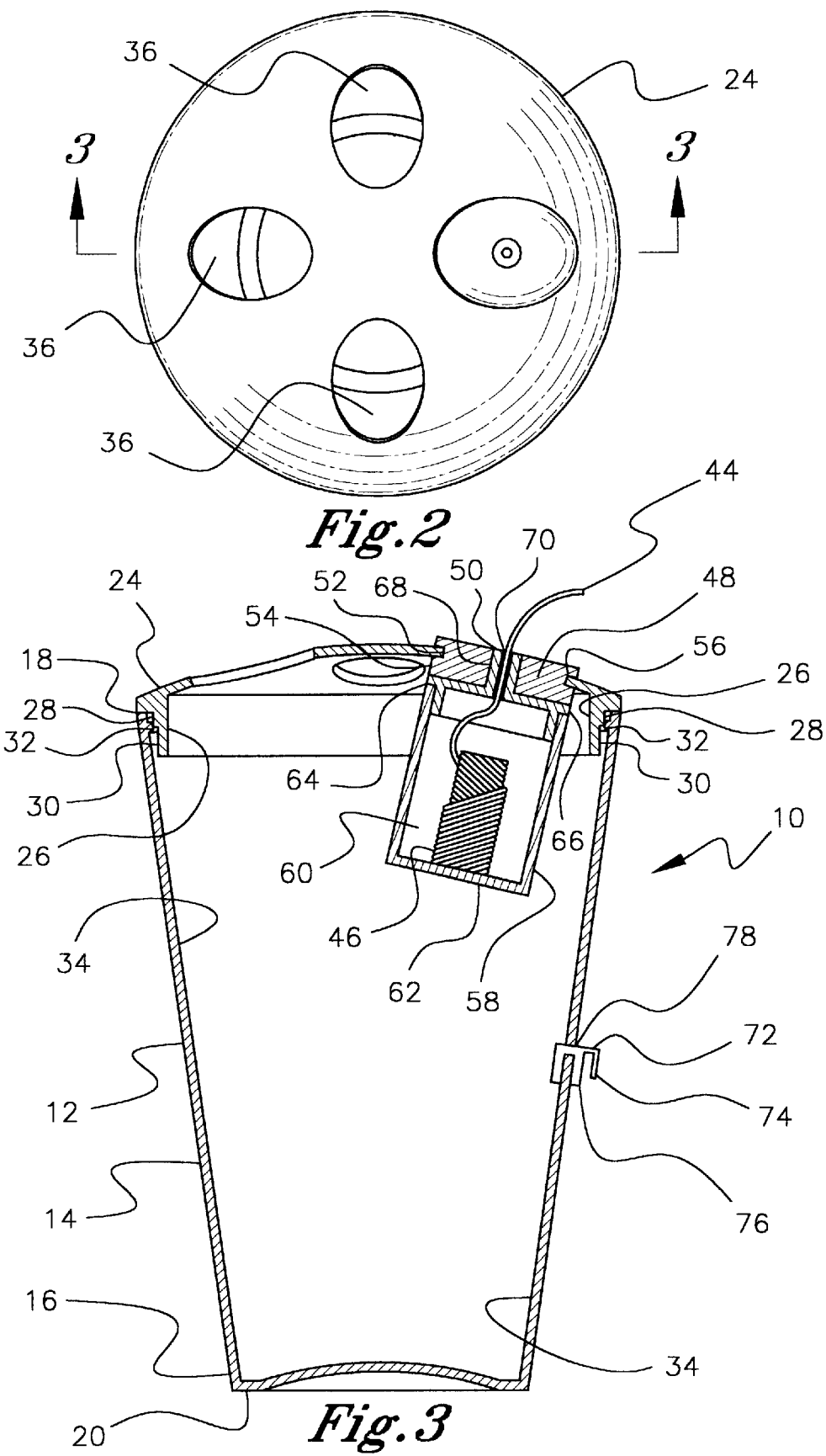

COMBINATION TOOTHBRUSH HOLDER AND DENTAL FLOSS DISPENSER

BACKGROUND OF THE INVENTION

1. Field of the Invention

This invention relates to dental hygiene. More particularly, it relates to an apparatus for retaining a toothbrush and roll of dental floss for use in cleaning someone's teeth and otherwise maintaining healthy dental hygiene.

2. Description of Prior Art

Dental hygiene products are well known in the prior art. Many products exist for use in dental hygiene and include, for example, toothbrushes, toothpicks, toothpaste, mouthwash, rinsing cups and dental floss. These products are typically stored in a convenient location proximal to a bathroom sink so that an individual can easily clean their teeth and otherwise maintain healthy dental hygiene.

Those individuals concerned with the aesthetic setting of their bathroom may wish to conceal or organize their dental hygiene products instead of placing them upon the counter-top of their bathroom sink area. Of course, some people simply store their dental hygiene products within a cabinet mounted above the bathroom sink. However, in doing so, many people forget to clean their teeth in that the dental hygiene products are not prominently displayed. In this regard, organizers for dental hygiene products have been invented which prominently display the dental hygiene products within an individual's visual proximity. Some of these inventions are drawn to a single dental hygiene product, such as those inventions shown in U.S. Pat. Nos. 5,490,722 to Sonnett et al. and 5,765,739 to Yates, III which disclose dental floss dispensers. Both of these inventions are limited to dental floss dispensers and do not suggest or teach an apparatus in combination for use with other dental hygiene products such as a toothbrush. Also seen in the prior art are toothbrush holders which usually include a housing with a lid having a plurality of holes formed in a top end. The elongated toothbrush handle inserts through one of the holes thereby retaining the brush in an upright position such that the bristles of the toothbrush are disposed above the housing and permitted to dry. These inventions too fail to suggest or teach an apparatus in combination for use with other dental hygiene products such as a roll of dental floss.

The above aforementioned devices are deficient in many ways. Most noticeable is that each of these prior art devices merely permit an individual to organize a single dental hygiene product. Accordingly, if an individual wants to organize a plurality of objects, one must provide a multitude of organizers. This unfortunately clutters the counter-top of an individual's bathroom sink and defeats the purpose of providing an aesthetically pleasing and organized bathroom area. Therefore, improvements on dental hygiene product organizers have been invented.

U.S. Pat. No. 4,978,003 to Foster discloses one type of combination organizer. Shown therein, is a housing having an inner cavity for receiving a disposable rinsing cup. Disposed along a top side of the housing is a lid having a plurality of holes formed therein for receiving and retaining toothbrushes in an upright position. Unfortunately, this invention fails to disclose anything that would permit other dental hygiene products to be organized within the invention, such as, for example, a roll of dental floss.

Some inventions found in the prior art attempt to provide an organizer that stores a plurality of items including, a toothbrush, toothpaste, dental floss and other dental hygiene products. Such can be seen in U.S. Pat. Nos. 5,215,193 to Dennis, 5,662,130 to Wiltshire and 5,638,840 to Lee et al. However, these inventions have also proven to be deficient. The most evident deficiency relates to the complicated structure and the need for a plurality of parts to form the device. Accordingly, these devices are difficult to market since the high manufacturing costs substantially outweigh the marketing price. Simply put, individuals avoid purchasing these products since they cost too much. Further, not everyone wants an organizer that can hold every dental hygiene product known. Many individuals simply want a device that can retain a toothbrush and a roll of floss.

Recognizing a desire for a device which merely holds a toothbrush and roll of floss, certain prior art devices have been invented which attempt to fulfill this simple desire. Such can been seen in U.S. Pat. Nos. 4,673,106 to Fishman, 5,097,964 to Fitz, 5,335,798 to Bonwell, and 5,924,429 to Morando. However, these devices, like others in the prior art, have shown to possess major deficiencies which warrant improvements to made thereupon. Again, as seen before, these devices employ a multitude of parts, making them difficult to manufacture and therefore expensive to market. Further, some have gone as far as to employ electrical signaling means, such as that shown in U.S. Pat. No. 5,335,798, for the purpose of reminding the user to floss. These type of devices have shown to complicate even further a simple concept which is merely that an individual should remember to floss their teeth after brushing.

From all of the prior art references, it is clear that an improved dental hygiene product is needed. The improved device should avoid the use of any electrical signaling means and employ as few parts as possible. This would ensure low manufacturing costs. The improved dental hygiene product device should also provide organization for just a few dental hygiene products, such as, for example, a toothbrush and a roll of dental floss.

SUMMARY OF THE INVENTION

I have invented an improved dental hygiene product which overcomes the deficiencies seen in the prior art. My device employs only a few parts and is therefore easy and inexpensive to manufacture. Further, my device provides for the organization of only a few dental hygiene products—namely, a toothbrush and a roll of dental floss. Each product is retained by my improved device in a small cup-like shaped housing which is designed to rest upon a bathroom sink counter-top such that it is both unobtrusive, easy to access, and aesthetically pleasing to the eye.

A bottom member is shaped like a cup with a flat bottom portion and a circular open top portion. A convexed-shaped top fits in the bottom member open top portion and has a plurality of holes formed therein. The holes can receive an elongated portion of a toothbrush. One of the holes has a rubber grommet wedged within the hole. The grommet has a hole formed in a middle portion thereof. A small housing enclosing a roll of dental floss mounts below the grommet. The small housing further includes a top with a tip portion which fits within the hole formed in the grommet. The dental floss threads through the tip portion and the hole of the grommet to provide its user access to the dental floss. A small cutter is attached along an outer circumference of the bottom portion and is used to cut a strand of desired length of dental floss.

BRIEF DESCRIPTION OF THE DRAWINGS

The invention may be best understood by those having ordinary skill in the art by reference to the following detailed description when considered in conjunction with the accompanying drawings in which:

FIG. 2 is a top plan view of the preferred embodiment of the present invention;

FIG. 3 is a cross-sectional view along lines 3—3 of FIG. 2;

DETAILED DESCRIPTION OF THE INVENTION

Figure 1:
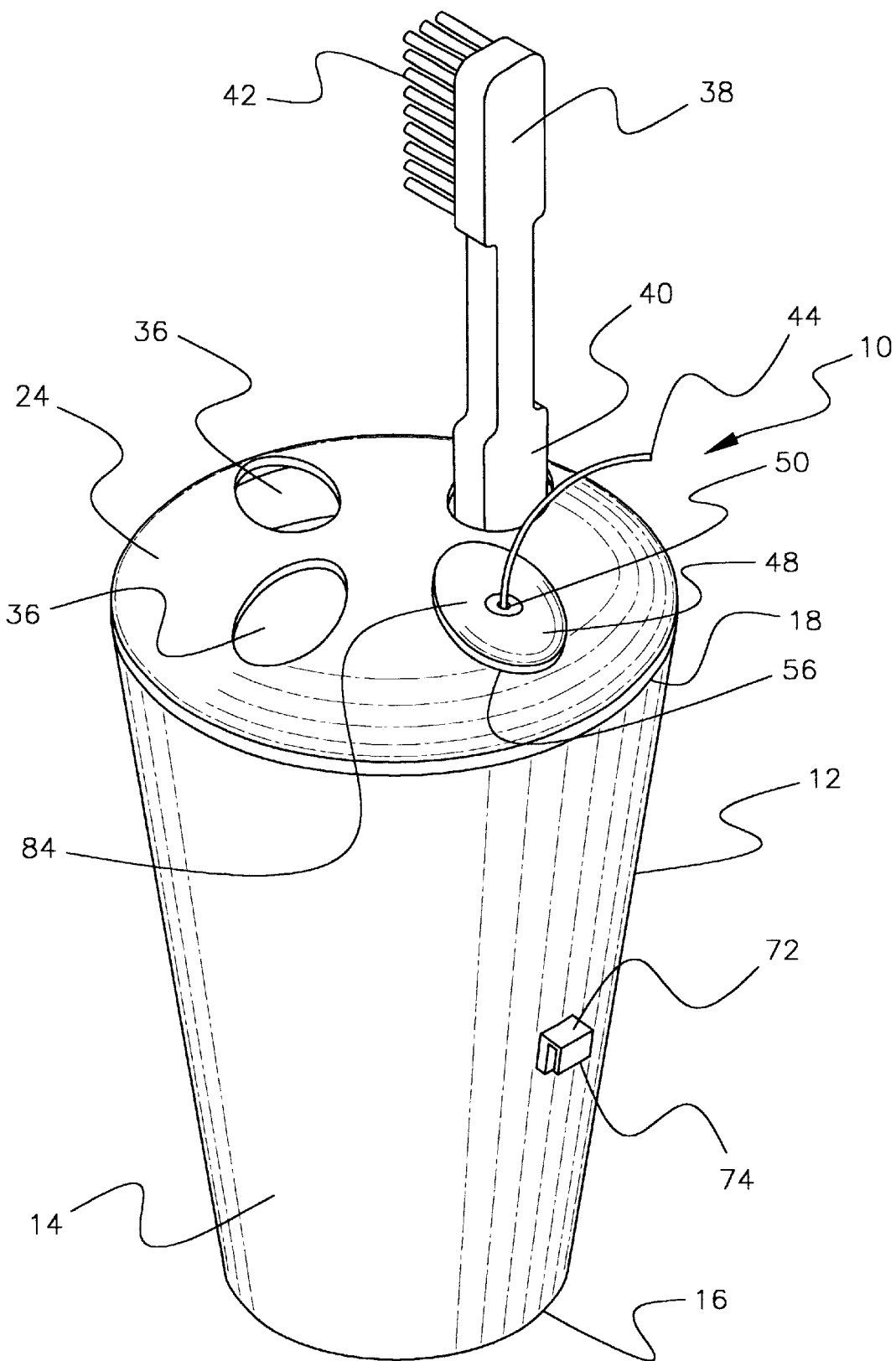
FIG. 1 is a perspective view of a preferred combination toothbrush holder and dental floss dispenser of the present invention.

Throughout the following detailed description, the same reference numerals refer to the same elements in all figures.

Referring to FIG. 1, a combination toothbrush holder and dental floss dispenser apparatus 10 of the present invention is shown. Apparatus 10 of FIG. 1 represents the preferred embodiment of the present invention. However, alternate embodiments exist and will be discussed in further detail hereinafter. Apparatus 10 includes a bottom member 12 having a cup-like shape, also known as a frusto-conical shape. In accordance therewith, bottom member 12 has a circular outer circumference 14 which has a smaller diameter at a bottom end 16 then that at a top end 18.

Figure 4:
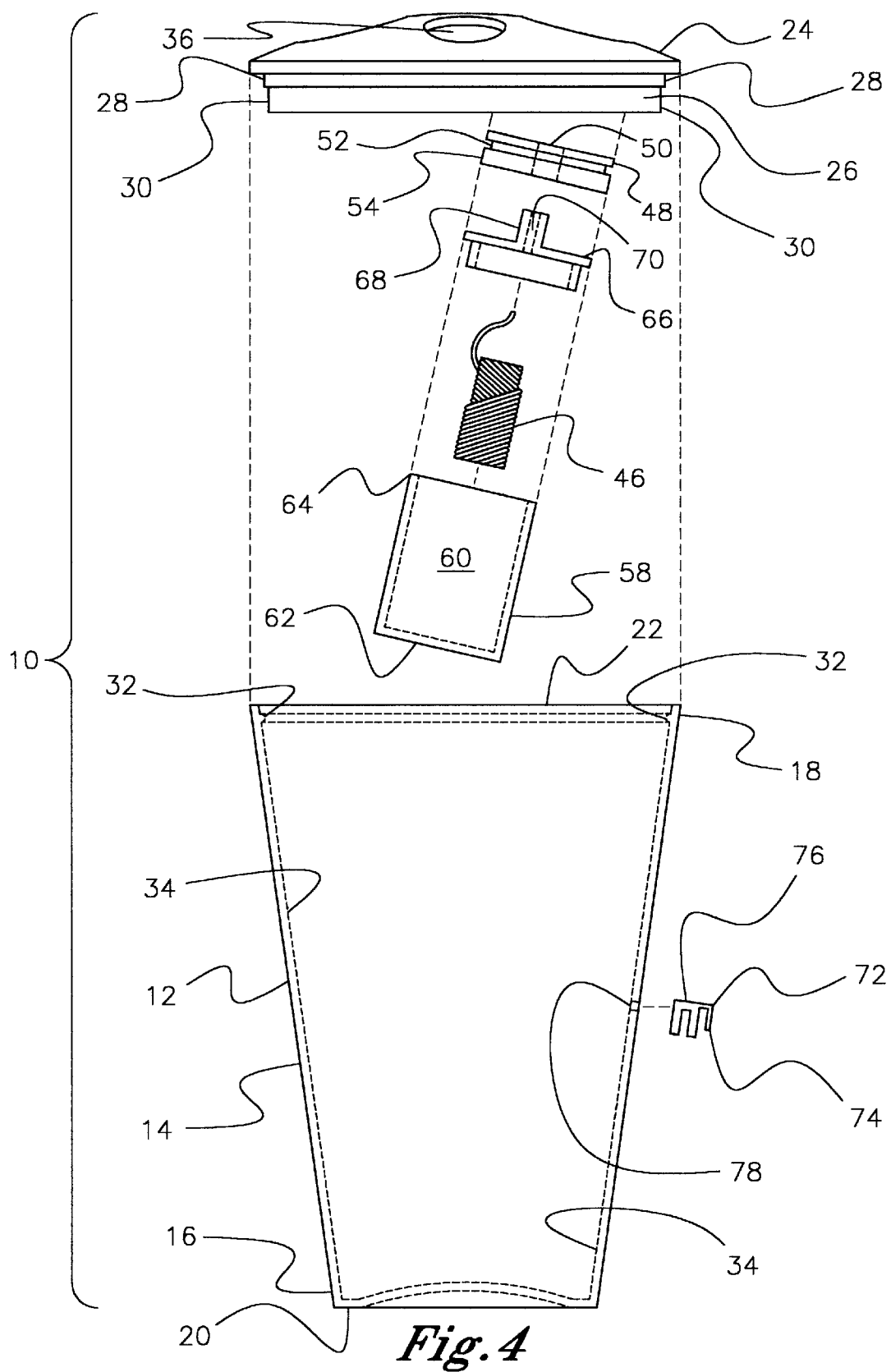
FIG. 4 is an exploded view of the preferred embodiment of the present invention.

Referring to FIG. 4, it is shown that bottom end 16 includes a flat bottom rim 20 which is used to rest upon a planar surface, such as, for example, a bathroom sink counter-top. Top end 18 includes an circular open top portion 22. A lid 24 having a downwardly extending circular integral two-part skirt 26 fits within circular open top portion 22. Lid 24 is retained by friction within open top portion 22. The two-part skirt 26 has a first part 28 and a second part 30 wherein first part 28 has a greater diameter than second part 30. As shown in FIG. 3, first part 28 rests upon a ledge 32 formed within an inner surface 34 of bottom member 12 when lid 24 inserts within open top portion 22.

Referring to FIG. 1, it is shown that lid 24 has a plurality of holes 36 formed therein. In the preferred embodiment, four holes are provided and have a generally oval shape. Holes 36 can be used to receive and retain a toothbrush 38 in an upright position. In particular, an elongated handle portion 40 of toothbrush 38 inserts through one of the holes 36 such that bristles 42 are exposed to the ambient air for the purpose of drying after each use.

With continuing reference to FIG. 1, it is shown that a strand 44 from a source of dental floss 46 (see FIG. 3) is provided with apparatus 10. In particular, one of the holes 36 is plugged with a grommet 48 having a center aperture 50 formed therethrough. With reference to FIGS. 3 and 4, it is shown that grommet 48 has a groove 52 formed along an outer surface 54 which mates with a circumference 56 of hole 36. It is therefore understood that grommet 48 has generally the same shape as hole circumference 36 when it is inserted within hole 36. The strand 44 from the source of dental floss 46 threads through aperture 50.

With reference to FIGS. 3 and 4, it is shown that the source of dental floss 46 (usually a spool or roll) is disposed within a small housing 58 mounted below grommet 48. Housing 58 has an inner cavity 60 in which the source of dental floss 46 is retained. Housing 58 has a closed bottom end 62 and an open top end 64 on which a cover 66 inserts thereover, retained by a friction fit. Cover 66 has an upwardly extending tip portion 68 which inserts within grommet aperture 50. Cover tip portion 68 also has a center aperture 70 formed therethrough which axially aligns with grommet aperture 50. Accordingly, the strand 44 from the source of dental floss 46 threads through both the cover tip portion aperture 70 as well as grommet aperture 50.

Referring back to FIG. 1, it is shown that a cutter element 72 is disposed along bottom member outer circumference 14, preferably below grommet 48. Cutter element 72 includes a sharpened portion 74 integral with a clip portion 76 which inserts within an opening 78 formed through bottom member outer circumference 14. Clip portion 76 is retained by a "snap-in" type friction fit. Cutter element 72 is used to cut a strand 44 of desired length from the source of dental floss 46. In particular, an individual would pull on strand 44 with their fingers thereby unraveling a length of dental floss. When the desired length has been pulled from housing 58, strand 44 is looped around cutter element sharpened portion 74, whereafter force is applied in a direction away from cutter element 72 such that strand 44 is cut. Thereafter, strand 44 can be used to floss the individual's teeth.

Figure 5:
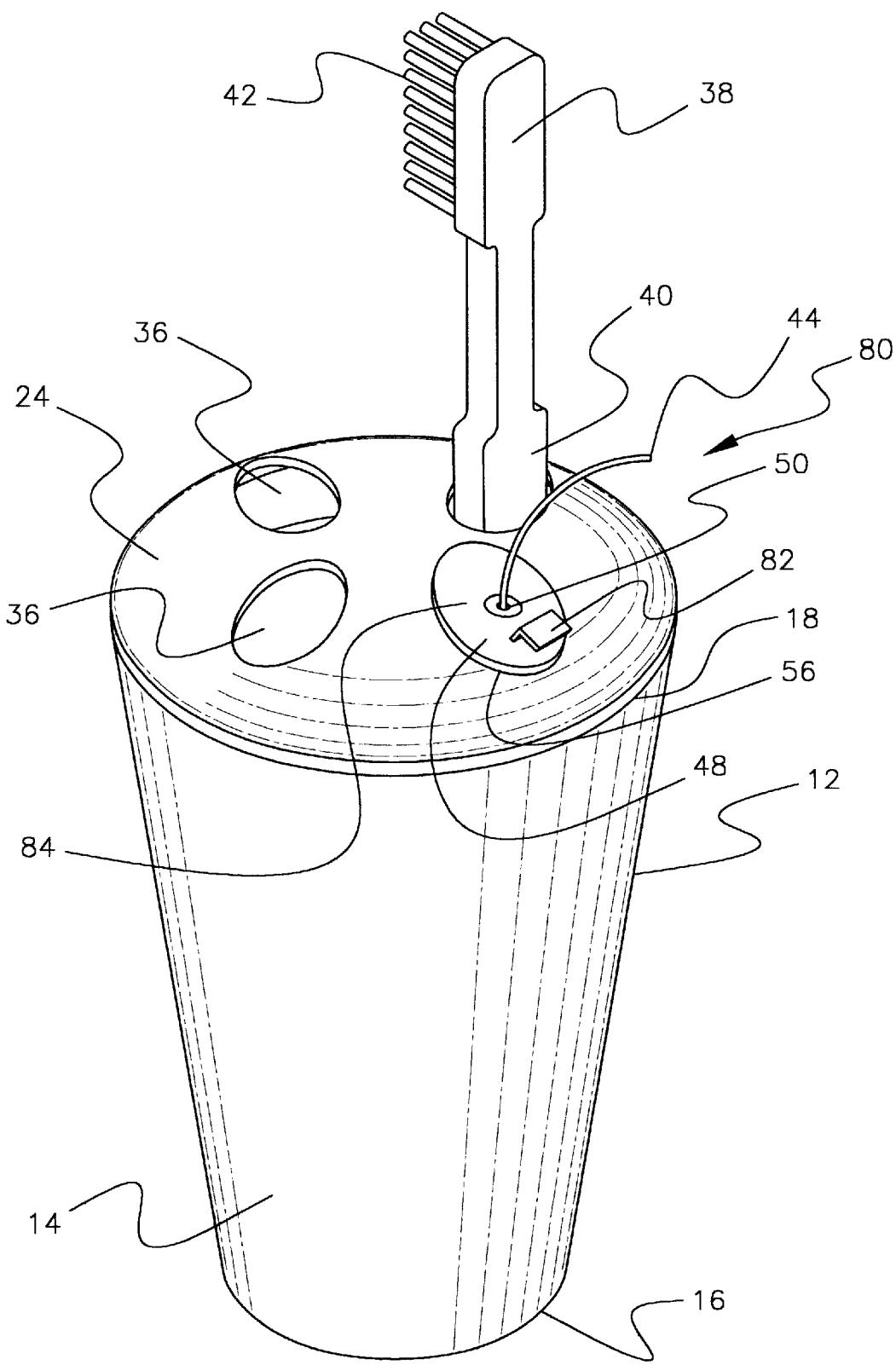
FIG. 5 is an alternate embodiment of the present invention.

Referring to FIG. 5, an alternate embodiment of the present invention is shown wherein a combination toothbrush holder and dental floss dispenser apparatus is designated as 80. Apparatus 80 is similar in structure to apparatus 10 with one major exception. In regards thereto, apparatus 80 has a cutter element 82 mounted proximal to aperture 50 on a top surface 84 of grommet 48.

Equivalent elements can be substituted for the ones set forth above such that they perform the same function in the same way for achieving the same result.

Having thus described the invention what is claimed and desired to be secured by Letters Patent is:

1. A dental hygiene product organizer comprising:
   a) a frusto-conical shaped bottom member having a closed bottom end and an open top end, the bottom end having a smaller diameter than the top end;
   b) a removable lid inserted within the bottom member open top end and having a top surface and a plurality of holes formed therethrough;
   c) a grommet inserted within one of the plurality of holes formed through the lid and having a center aperture formed therethrough;
   d) a housing disposed beneath the grommet and having an inner cavity, a closed bottom end and an open top end, the open top end having a removable cover inserted therewithin, the cover having an upwardly extending tip portion, the tip portion having a center aperture formed therethrough, the tip portion inserted within the grommet center aperture such that the tip portion center aperture axially aligns with the grommet center aperture;
   e) a source of dental floss enclosed within the housing inner cavity and having a first end inserted through the cover tip portion center aperture and out through the grommet center aperture;
   f) a cutter element mounted on the organizer for removing a strand from the first end of the source of dental floss; and
   g) the holes for receiving and retaining an elongated portion of a toothbrush such that bristles of the toothbrush are exposed to ambient air.

2. The dental hygiene product organizer of claim 1, further comprising the bottom member having an outer circumference and a vertical axis perpendicularly disposed to the outer circumference.

3. The dental hygiene product organizer of claim 2, wherein the bottom member bottom end has an annular rim portion disposed along a bottom side outer edge and a concave center portion disposed within the annular rim portion, the annular rim portion providing a means for positioning the organizer in an upright position.

4. The dental hygiene product organizer of claim 1, wherein the lid top surface is convexed-shaped.

5. The dental hygiene product organizer of claim 4, further comprising:
   a) the lid having a skirt portion, a bottom surface and an outer edge, the skirt portion downwardly extending from the bottom surface proximal to the outer edge;
   b) the bottom member having an inner surface and a ledge formed therein proximal to the open top end; and
   c) the lid skirt portion mating with the bottom member ledge creating a friction fit therebetween when the lid is inserted within the bottom member.

6. The dental hygiene product organizer of claim 1, wherein the plurality of holes formed through the lid comprises four holes.

7. The dental hygiene product organizer of claim 1, wherein each of the plurality of holes formed through the lid are generally oval-shaped.

8. The dental hygiene product organizer of claim 1, further comprising:
   a) each of the plurality of holes formed through the lid having an inner edge;
   b) the grommet having an outer surface and a groove formed therearound; and
   c) the grommet groove mating with the inner edge of one of the plurality of holes when the grommet is inserted therewithin.

9. The dental hygiene product organizer of claim 1, wherein the housing disposed beneath the grommet is cylindrically-shaped.

10. The dental hygiene product organizer of claim 1, wherein the source of dental floss comprises a spool of dental floss.

11. The dental hygiene product organizer of claim 1, further comprising:
    a) the cutter element having a clip portion and a sharpened portion;
    b) a hole formed in the bottom member below the grommet; and
    c) the cutter element clip portion inserted within the bottom member hole such that the cutter element is retained by a friction fit.

12. The dental hygiene product organizer of claim 1, further comprising:
    a) the grommet having a top surface and a slit formed therethrough proximal to the grommet center aperture;
    b) the cutter element having a clip portion and a sharpened portion; and
    c) the cutter element clip portion inserted within the slit formed in the grommet.

13. A combination toothbrush holder and dental floss dispenser apparatus comprising:
    a) a frusto-conical shaped bottom member having a closed bottom end, an open top end, an outer circumference, an inner surface, a ledge formed along the inner surface proximal to the open top end and a vertical axis perpendicularly disposed to the outer circumference, the bottom end having a smaller diameter than the top end;
    b) a removable lid inserted within the bottom member and having a top surface, a plurality of holes formed therethrough, a skirt portion, a bottom surface and an outer edge, the skirt portion mating with the bottom member ledge creating a friction fit therebetween when the lid is inserted within the bottom member, each of the plurality of holes having an inner edge;
    c) a grommet having a center aperture formed therethrough, an outer surface and a groove formed in the outer surface, the groove mating with the inner edge of one of the plurality of holes when the grommet is inserted therein;
    d) a housing disposed beneath the grommet and having an inner cavity, a closed bottom end and an open top end, the open top end having a removable cover inserted therewithin, the cover having an upwardly extending tip portion, the tip portion having a center aperture formed therethrough, the tip portion inserted within the grommet center aperture such that the tip portion center aperture axially aligns with the grommet center aperture;
    e) a source of dental floss enclosed within the housing inner cavity and having a first end inserted through the cover tip portion center aperture and out through the grommet center aperture;
    f) a cutter element mounted on the organizer for removing a strand from the first end of the source of dental floss; and
    g) the holes for receiving and retaining an elongated portion of a toothbrush such that bristles of the toothbrush are exposed to ambient air.

14. The combination toothbrush holder and dental floss dispenser apparatus of claim 13, wherein the bottom member bottom end has an annular rim portion disposed along a bottom side outer edge and a concave center portion disposed within the annular rim portion, the annular rim portion providing a means for positioning the organizer in an upright position.

15. The combination toothbrush holder and dental floss dispenser apparatus of claim 13, wherein the lid top surface is convexed-shaped.

16. The combination toothbrush holder and dental floss dispenser apparatus of claim 13, wherein the plurality of holes formed through the lid comprises four holes.

17. The combination toothbrush holder and dental floss dispenser apparatus of claim 13, wherein each of the plurality of holes formed through the lid are generally oval-shaped.

18. The combination toothbrush holder and dental floss dispenser apparatus of claim 13, wherein the housing disposed beneath the grommet is cylindrically-shaped.

19. The combination toothbrush holder and dental floss dispenser apparatus of claim 13, further comprising:
    a) the cutter element having a clip portion and a sharpened portion;
    b) a hole formed in the bottom member below the grommet; and
    c) the cutter element clip portion inserted within the bottom member hole such that the cutter element is retained by a friction fit.

20. The combination toothbrush holder and dental floss dispenser apparatus of claim 13, further comprising:
    a) the grommet having a top surface and a slit formed therethrough proximal to the grommet center aperture;
    b) the cutter element having a clip portion and a sharpened portion; and
    c) the cutter element clip portion inserted within the slit formed in the grommet.

* * * * *